United States Patent
Leonov et al.

(10) Patent No.: US 6,179,778 B1
(45) Date of Patent: Jan. 30, 2001

(54) COMPUTERIZED METHOD OF HEALTH PROPHYLAXIS THROUGH FOOD COMBINING MICROCOMPUTER FOR FOOD COMBINING SOFTWARE PRODUCT FOR FOOD COMBINING

(76) Inventors: Valery Leonov; Pavel Leonov, both of 47-2-137, Vitebsky Street, St. Petersburg (RU), 196233

( * ) Notice: Under 35 U.S.C. 154(b), the term of this patent shall be extended for 0 days.

(21) Appl. No.: 09/230,925

(22) PCT Filed: Aug. 26, 1996

(86) PCT No.: PCT/IB96/00827

§ 371 Date: Feb. 1, 1999

§ 102(e) Date: Feb. 1, 1999

(87) PCT Pub. No.: WO97/32269

PCT Pub. Date: Sep. 4, 1997

(51) Int. Cl.$^7$ ...................................................... A61B 5/00
(52) U.S. Cl. .............................. 600/300; 705/2; 128/898
(58) Field of Search ................................ 434/127; 703/11; 705/2–3; 708/132–133; 600/300–301; 128/700, 920–925, 897–898

(56) References Cited

U.S. PATENT DOCUMENTS

| 5,691,927 | * | 11/1997 | Gump | 708/131 |
| 5,692,501 | * | 12/1997 | Minturn | 128/920 |
| 5,704,350 | * | 1/1998 | Williams, III | 128/921 |
| 5,836,312 | * | 11/1998 | Moore | 128/897 |
| 5,954,640 | * | 9/1999 | Szabo | 600/300 |

* cited by examiner

*Primary Examiner*—Cary O'Connor
*Assistant Examiner*—Michael Astorino

(57) ABSTRACT

An apparatus and method for health prophylaxis through food combining. Using an electronic multi-food combining table to recommend nutritional quality of food stuff combinations consumed. Recommendations are based on observations over a 3–4 hour period after meals are digested.

12 Claims, No Drawings

COMPUTERIZED METHOD OF HEALTH PROPHYLAXIS THROUGH FOOD COMBINING MICROCOMPUTER FOR FOOD COMBINING SOFTWARE PRODUCT FOR FOOD COMBINING

BACKGROUND OF THE INVENTION

The knowledge accumulated by people on food combining is most systematically reflected and approved by Dr. Shelton: Dr. Herbert M. Shelton "Food Combining Made Easy", 1951 Dr. Herbert M. Shelton "The Science and Fine Art of Food and Nutrition", 6th rev.ed. (Hygienic System, v.2), 591pp il pa 1984, Natural Hygiene Press.

Dr. Shelton summed up this knowledge in his famous table which we completely reproduce on the next page as the basis of the invention proposed hereby.

The volume of the knowledge on Food Combining is large enough to be used by an ordinary man in his health prophylaxis going just by the printed materials on the subject, yet we have not encountered any attempts to computerize such health prophylaxis for ordinary people. Hence we are trying to make such a step. We claim a group of three closely connected inventions consisting of the Method and the Technical Facilities developed particularly to implement the said Method as stated hereabove.

tion and producing unnecessary fermentation in the stomach and in the intestines. Stomach distress (heart burn), gases, belching (eructation) and mucus flows are the notoriously known signs of such fermentation. Incorrect food combinations at a single meal cause fermentation and putrefaction which produce, as a result of bacterial decomposition, such products as carbonic acid gas, spiritus, ammonia, acids etc. In order to neutralize, insulate and take out these poisons the human body has to waste its vital reserves. Incorrect food combinations not only fail to increase the stock of power and vitamins, but even deprive the organism of the existing stocks. The fact is, when poison accumulation exceeds the body's capability to neutralize it, the body's reserves are wasted on elimination the toxins. The prolonged struggle between the body and the indigestive food combinations or with poisonous products of bacterial decomposition sooner or later weakens the body. It is the incorrect nutrition that causes enormous waste of vital power and physiological reserves, which could otherwise be used later on. These reserves are especially vital for elderly people who are weaker anyway and whose rehabilitation capabilities are hindered. With the body's reserves carefully controlled, according to Dr. Shelton, people could outlive 100 years still preserving a juvenile enthusiasm and energy.

This view of Dr. Shelton, the doctor of 9 sciences, author of 40 research works, is supported not only by pure scientific Dr. Shelton's "Food Combining Table"

|  | Protein | Starch | Fat | Sweet Milk | Sour Milk | Non-Starchy Vegetables (cooked) | Salad or Raw Green Vegetables | Acid Fruits | Sub-Acid Fruits | Sweet Fruits (Dried) | Melons |
|---|---|---|---|---|---|---|---|---|---|---|---|
| Protein | bad | bad | bad | bad | bad | good | good | poor* | bad | bad | bad |
| Starch | bad | good | good | bad | bad | good | good | bad | fair | poor | bad |
| Fat | bad | good | good | fair | fair | good | good | good | good | good | bad |
| Sweet Milk | bad | bad | good |  |  | poor | poor | fair | fair | bad | bad |
| Sour Milk | bad | bad | good |  |  | poor | poor | fair | fair | fair | bad |
| Green Vegc.† | good | good | good | poor | poor | good | good | poor | fair | poor | bad |
| Sub-Acid Fruits† | bad | bad | good | fair | fair | poor | poor | good | good | good | fair |
| Acid Fruits | bad | bad | good | fair | fair | fair | fair | good | good | poor | fair |
| Sweet Fruits‡ | poor | poor | good | poor | fair | poor | poor | poor | good | good | fair |
| Melons | bad | bad | bad | bad | bad | bad | bad | bad | fair | fair | good |

*Acid fruits are fair with nuts.
†Raw or cooked.
‡Dried

SUMMARY OF THE INVENTION

In order to define the subject of the proposed invention, depict consistently the technical problem of "Health Protection through Food Combining" and outline its solution we should give some brief information from Dr. Shelton's works.

According to Dr. Shelton, Food Combining covers a combination of scientific and practical facts testifying that digestion goes by the laws of physiology and biochemistry, which make it necessary to take into account some known physiological limitations of digestion, enzymes and gastric juice every time we are planning some food combinations for a single meal. The main problem is that people do not get health, strength and benefit from what they are eating, but from what their bodies can digest and assimilate. The correct food combinations for a single meal facilitate an easy assimilation of food in the stomach, while incorrect food combinations for a single meal make obstacles in food assimilation thus increasing time of digestion and assimilainvestigations of famous scientists like the famous physiologist academician I.Pavlov, but also by half a century of his personal non-medicamental experience as a practitioner. Tens of thousands of patients went through his would-famous "Health School". His works have been translated nearly into all languages of the world.

To this very subject the proposed invention refers. We take into consideration that ordinary people are little concerned about "digestive restrictions" and "physiological reserves".

Even though Dr. Shelton made a significant step to solve the problem, having compiled a table on the basis of his predecessor and colleague's works, but it did not make the problem easier for ordinary people. The authors of the proposed invention have been personally using this table for many years and got aware of all the problems related to it. It was the amazing results of "Health Prophylaxis Through Food Combining" that made us bear all the difficulties. The main aspects of the problem were: first, each time we had to recollect, for example, which products are proteins and which are carbohydrates, whether they are "concentrated" or not, second, which mark ("good", "poor" etc.) Dr. Shelton would give to every pair combination of products and, third, which marks he would give the food products cooked for a particular meal, as his table does not include any complicated combinations (3 or more products). Willingly or not, we wished we could pass over all those speculations to the computer, leaving only the final decision for people to be made (deciding whether it was "good" or "bad"), and the amazing results of the prophylaxis.

In ancient times ordinary people unconsciously followed the rules of "Health Prophylaxis through Food Combining" by following the habits and customs of their tribes. Let's take as an example a combination from Dr. Shelton's table. Proteins and carbohydrates make a "bad" combination. Now it is a scientifically proven fact, very often ignored by ordinary people, although in the older times it was strictly obeyed. Dr. Shelton cites a rule that existed in Ancient Greece and said that the warriors were forbidden to take meat and bread at a single meal. A similar quotation was found by him in old Hebrew Moses' Scripture. Dr. Shelton remarks that the very fact of including such a habit into the Holy Scripture, which was equal to sanctifying it by the God, proves that this habit was firmly followed. In the 20th century, though, the old habits of "Health Prophylaxis through Food Combining" are basically forgotten, with very few exceptions.

At present "Health Prophylaxis through Food Combining" is based on the above-shown Dr. Shelton's table, as well as on other printed books and on the numerous recipes from cookery books whose authors do take into consideration the principles of "Food Combining". In other words, today's technology is a "bookish technology", with its unavoidable difficulties, especially for ordinary people. The main 2 problems which we are trying to solve with our Method and our Technical Facilities are:

the person who is willing to follow the rules of Food Combining to strengthen his health has either to keep in his memory Dr. Shelton's table along with other recommendations and recipes, or he has to have all these books available every time he lays his dinner table or every time he goes to the restaurant;

Dr. Shelton's table estimates only the combinations of 2 food products, while the combinations of 3 or more food products are not represented in the table. This, again, makes the users either recollect the mathematical combinatory methods, or stick to no more than 2 food products at a meal, which is no longer used.

These two technological problems are quite difficult for ordinary people to solve, so "the bookish way" of health prophylaxis is not of any help for them. "Food Combining", if they ever heard the term, is no more than scientific meditations totally useless for in their everyday life. The results of "Health Prophylaxis through Food Combining" are available to an exclusively small group of people, so the knowledge on Food Combining does not come to light. Due to this negligence man's health (or at least that of the larger part of mankind) suffers drastically. Even if we present every single person on the Earth a free copy of Dr. Shelton's table and explain how good Food Combining is for their health, nothing will be changed in the current status quo, as "bookish" ways are normally foreign to ordinary people. This is the essence of the problem. It is rather of technological character, hence it can be solved only by technical means, which is the aim of the proposed invention.

People had to learn the Multiplication Table until the Calculator was designed. Now people are unlikely to be willing to learn the Food Combining Table, although it might be more important for them than the Multiplication Table as it concerns their health. This (exigency) of mankind should be facilitated with microprocessors to free people from the necessity of learning by heart the Food Combining Table and the accompanying definitions, terms and rules. The user of the calculator does not have to learn the theory of figures he is satisfied with the result of calculations, leaving the theory of figures for the designers of the calculator.

The Food Combining Table should be processed in the same way: a new microcomputer should be designed on the basis of all relevant definitions, terms and rules, while the user must obtain only the final product—the marks ("bad", "poor", "fair", "good") for the digestive quality of the food combination he is going to take. The microprocessor should also be able to assess the food combination regardless the quantities used—the user should be free to decide how many food products he is going to take at a particular meal. The proposed "Microcomputer for Food Combining" is intended to suit these purposes.

The problem of "Health Prophylaxis through Food Combining" is many-sided. It covers quite a number of such complicated notions as "natural food products and man's natural digestive capabilities", "food combinations invented by food manufacturers and the habits acquired by food consumers", "value added profit for food processors and health losses for their consumers", "flexibility of businessmen's mind and inertness of ordinary people's thinking". This tight knot of problems only man himself can unbind, but he must have an instrument to do it. The proposed "Microcomputer for Food Combining" is just this type of instrument.

The problem of "Health Prophylaxis through Food Combining" is many-sided. To spread a certain type of scientific knowledge we should introduce it into the "toy" series which are of an increasing rate of difficulty. The man who has mastered a pocket calculator is likely to get interested in a home computer, and then—in a professional computer. The scientific value of Food Combining is high enough to be spread widely. To implement it, we need an initial easy "toy". What is no less important, though, is the cost of the "toy". It should be of low cost otherwise we cannot expect it to be widely distributed, and correspondingly, we cannot count on the knowledge on Food Combining to be spread, either. Only with the inexpensive technical facilities the knowledge on Food Combining will come to light, it will be discussed by ordinary people who will get accustomed to it, which, in its turn, will arise interest in "Health Prophylaxis through Food Combining". The "Microcomputer for Food Combining" proposed herein is comparable in cost to an ordinary pocket calculator and can be used as such an easy "toy" for learning the rules of Food Combining.

The "Food Combining Microcomputer" looks like an ordinary pocket calculator, too: a similar LCD, a solar battery with an electrical power accumulator, and a keyboard. Only the signs on the keys are different, but, again, they are quite clear for everybody: "Vegetables", "Fish", "Butter", "Fruits" etc. After pushing one, two, three, ten or more keys, the user can push the key "Mark" (which is the "mark" of the digestive quality of the food selected) and see immediately the result on the display: "bad", "poor", "fair", or "good". Now the Microcomputer's part is over, and the user has to take a decision himself whether he will take the food products he has chosen at a single meal, as his habit goes, or plan his meal in a different way. Having thought of it once, the user will come to his "Food Combining Microcomputer" time and again.

Man is incredulous, but he is also curious. It goes without saying, he holds his health dear. These two features should drive him to practical measures, especially so because he has a "toy" to implement them. Why not observe one's state, if the Manual on "Microcomputer for Food Combining" says:

"If 3 or 4 hours after a meal you are feeling the signs of fermentation in your intestines, like stomach distress (heart burn), gases, belching or mucus flows, avoid eating the food combinations which are estimated "bad" and "poor". Observe how you are feeling. If you have never come across these symptoms and you consider yourself quite a healthy person, if you are sure your stomach and intestines are good enough, and your way of food consumption is rational, but the "Food Combining Microcomputer" shows from time to time a "bad" mark, you should exclude these food combinations from your ratio for a long enough period of time to check the real state of your health—who knows where your limit is?"

Man is a social being. A "toy" in the hands of one person arouses the curiosity of another. If you are feeling much better as a result of some steps undertaken, you are eager to share your experience with your friends and relatives. Slowly the scientific knowledge about the "Food Combining" will come to God's light from ignorance to attract those who have never before heard about it. This is the way for "Health Prophylaxis through Food Combining" opened by the "Microcomputer for Food Combining".

The authors of the present patent application call this way "COMPUTERIZED METHOD OF HEALTH PROPHYLAXIS THROUGH FOOD COMBINING" and claim the legal patent protection of the proposed Method, which in its healing effect is the same as the "bookish way", but with the specially designed Technical Facilities is becoming accessible to ordinary people, while ordinary people are, in a certain sense, the whole mankind.

"COMPUTERIZED METHOD OF HEALTH PROPHYLAXIS THROUGH FOOD COMBINING" is difficult in many aspects from developers' side. These difficulties are connected with the authors' concern about the implementation of their Method, which is discussed hereabove. For the users, however, the method is extremely simple. It enables the users:

to test regularly, before every meal, the digestive quality of the food in accordance with the Food Combining Criteria, to correct the nutrition process in accordance with short-time observations (3 or 4 hours after meals) of one's state with the target of eliminating the symptoms of gastric and intestinal fermentation, to correct the nutrition process on the basis of long-term observations of one's state with the overall target of improvement of one's health.

Utilization in this Method of the proposed "Microcomputer for Food Combining" enables even a seven-year-old boy to carry out the prophylaxis of his health, as for this he needs to know only two things:

the difference between the notions "good" and "bad", the fact that both man's health and man's illnesses have the same origin, which is the nutrition.

Definitely, the knowledge of these two things is possessed by everybody without any exception, which is the reason why mankind is ready to accept our Method of health prophylaxis.

Hereabove we set the technological task as for the Method and proposed the Technical Facilities specially designed as the technical solution. We disclosed hereabove the annovational idea which, definitely, needs a further development. The effectiveness of the further development depends upon the cooperation of the inventors of the Method with its users. In its turn, the cooperation depends on the legal basis it will obtain. The designer of the Method should obtain the money to further develop and implement the Method, while the user, in his turn, should pay for the license on utilization of the Method. Payment for the license constitute part of the price of the Technical Facilities, which should be worked out jointly by the manufacturer and the designer of the said Technical Facilities. This is possible only on condition of having a reliable legal basis, the starting point of which can be constituted by the claimed patent on the claimed proposed inventions.

DETAILED DESCRIPTION OF THE PREFERRED EMBODIMENT

Any computer technology is conglomeration of software and hardware. In the framework of our task it is unreasonable to design any special type of hardware, as there exist quite a number of suitable devices, as well as the corresponding technologies. We need only a appropriate algorithm and the software to implement it.

Pure transferring of the data on "Food Combining" from the printed materials onto the display is not the proper way to solve the problem—it is just another way of getting an electronic copy, which cannot help by itself. The main problem is not only transferring the information from the printed matters into the microprocessor, but also getting an opportunity to process the information. The data on "Food Combining" exists in verbal form, while the computer can only process the data presented in characters. Without any doubt, modern technologies in programming can facilitate the processing of the data presented in verbal form, too. The data on "Food Combining" is not an exception in this respect, either. But designing a special software for "Food Combining" to process more than two food products taken at a single meal will demand comparatively powerful technical facilities, and then the cost of manufacturing and selling such a product will be too high. The proposed "Computerized Method of Health Prophylaxis through Food Combining" is not targeted exclusively at wealthy people who can afford buying an expensive "toy". The proposed Microcomputer is intended for everyone, considering the fact that common people are prone to buy only useful and inexpensive "toys" like a pocket calculator.

To enable people to process the information on "Food Combining" with small microprocessors like a pocket calculator, we need an idea to transfer the data into characters in an unusually simple way. Dr. Shelton made his contribution here, too. He gives us a key for the best way to computerize his table to be used with small microprocessors. None of those who went to school will object to such equations as "good"="4" or "bad"="2" if we want to estimate the quality of something. So, with Dr. Shelton's key we can consider the task of processing two food product combinations settled. Let's make the next step—pass over from Dr. Shelton's two-dimensional table to multi-dimensional table for combinations of two and more products.

Any combination of three and more products can be represented as a set of certain pairs which have already been "marked" by Dr. Shelton. Since the table does not consider the weights of the products chosen, the mean proportional of the "marks" of the corresponding pairs can be used to calculate the necessary marks. This second step brings the complete solution to the problem of computerizing "Food Combining" with the help of small microprocessors. The proposed steps, indeed, result in a multi-dimensional table with the "marks" of the digestive quality of food combinations with two or more products. While Dr. Shelton's table is two-dimensional (two-product), it can be easily represented on a sheet of paper. This paper version of the table is the basis of the bookish way of health prophylaxis through food combining. Our table is multi-dimensional, it comprises many products that is why it can not be drawn on a sheet of paper. It is not reasonable to display it from the microprocessor where is it formed according to our algorithm, or to take it out from the computer's memory, where it was recorded in the process of its formation, or to take it out from the physical storage of the microprocessor where it was registered by the manufacturer. We think it necessary to stress here one point: our table is, in reality, an electronic table facilitating a transfer from "book technology" to "computer technology" in health prophylaxis through food combining. This fact now is clear both for a designer of microprocessors and for a designer of software.

Therefore, we think it logical to name our table "ELECTRONIC MULTI-FOOD COMBINING TABLE". Here we give another description of our table with its characteristic features compared to those of Dr. Shelton (see p.2).

Dr. Shelton's table can be called "Two-Product Combining Table". Its characteristic features are as follows:

it "marks" the digestive qualities of combinations of two classes of products ("proteins and starches", "proteins and fats" etc.).

"marks" are expressed in words.

Our "Electronic Multi-Food Combining Table" as compared to its prototype by Dr. Shelton is characterized with the following features:

it marks the digestive qualities of combinations of any number of products (Fish, Rice, Potatoes, Vegetable oil etc., both for these products taken separately and for their combinations with any other products - however imaginative modern cooks are!);

the "mark" in our microprocessor is given in the form of to a figure approximated to "5", "4", "3", or "2";

"the embryo" of the table is composed of the "Numeric Two Food Product Combining Table" which is worked out by a hygienist on the basis of Dr. Shelton's table and all the additional data which became known after the publication of Dr. Shelton's table, and also the data which will become known still later;

the said "embryo" of our table is introduced into the physical storage of the microprocessor for "Food Combining", or is introduced into the software as the initial database;

the "marks" for three or more food product combinations are processed by the microprocessor according to the following algorithm: any combination of three and more food products can be looked upon as a combination of pair combinations which are already stored in the "embryo" of the table. The "mark" for a three and more food product combination will be calculated as a mean proportional of the "marks" for the corresponding pair combinations.

In the next section the "Electronic Multi-Food Combining Table" is described again, this time with particular numeric examples.

A Better Way of Implementation of the Technical Facilities

For any geographical or ethnic region we can point out some 10 or 20 main food products, like "rice", "fish", "beans" etc. Let's call these products "A", "B", "C" and so on. According to the edited Dr. Shelton's table the "marks" to the digestive quality of these pair combinations are: 5", "4", "3", or "2".

As a result we have now the "embryo" of our electronic table:

| The "Embryo of the Electronic Table". | | | | | | |
|---|---|---|---|---|---|---|
| A | 5 | | | | | |
| B | 3 | 5 | | | | |
| C | 4 | 2 | 5 | | | |
| D | 5 | 3 | 2 | 5 | | |
| E | 2 | 2 | 5 | 4 | 5 | |
| . | . | . | . | . | . | . |
| | A | B | C | D | E | . |

The "Electronic Table" itself if formed by the software on the basis of the algorithm which can be illustrated by 2 examples:

EXAMPLE 1

A combination of 3 food products.

Let our combination comprise food products "A", "B", and "C". It can be considered as a set of 3 pair combinations: "A,B", "A,C", and "B,C". For every pair combination we take ready-made "marks" from the "Embryo of the Electronic Table".

$[A,B]=3, [A,C]=4, [B,C]=2$

The "mark" we need to evaluate our 3-product combination is calculated as the mean proportional of the three values:

$[A,B,C]=(3+4+2):3=3.0$

EXAMPLE 2

A combination of 4 food products.

Let our combination comprise food products "A", "B", "D", and "E". like in the previous example we take the pre-defined "marks" from the "Embryo of the Electronic Table:"

$[A,B]=3 \ [A,D]=5 \ [A,E]=2 \ [B,D]=3 \ [B,E]2 \ [D,E]=4$

Now we can calculate the "mark" for our 4-product combination:

$[A,B,D,E]=(3+5+2+3+2+4):6=3.2$

For any other possible combinations the calculations are done in a similar way. If the Technical Facility can take into consideration 10 food products, the "Electronic Multi-Food Combining Table" will hold about 1,000 figures. If it is necessary to "mark" up to 20 food products, the number of possible combinations will be about 1,000,000.

The examples given prove that there should not arise any problems as to programming or microprogramming, so in this respect we can consider the task of computerizing the knowledge on Food Combining practically solved. We have only to discuss better variants of the Technical Facilities for testing the digestive qualities of various food combinations which we are used to take at a single meal. This testing is to be done for the purpose of health prophylaxis through correct food combinations. Such technical facilities might be called "FOOD COMBINING TESTER".

The proposed hereby "Food Combining Microcomputer" is in fact an autonomous "Food Combining Tester" or, to be precise, a basic model of such a tester, since it fulfills the minimum scope of functions. It is such model of Tester with a minimal scope of functions that we consider the best version of "Food Combining Microcomputer", having the lowest production costs, hence the maximal sales volume. Here we come back to the fact that our inventive idea does not concern the Facilities, but the Method of health prophylaxis through the knowledge on Food Combining which is still lying in the shade. Again we must stress that the knowledge on Food Combining will continue lying in the shade until a comparatively cheap, yet useful "toy" becomes available to public at large. It is only such a "toy", being in their hands and stipulating them first just to use the word "Food Combining" that can bring this knowledge into the light. We are sure that Technical Facilities alone are not enough, and we must find an efficient way of prophylaxis, since people's minds and habits are extremely inertial as proven by many years of the authors' personal experience.

At the same time the second claimed Technical Facility—"Software Product for Food Combining" which can also be called "FOOD COMBINING PROGRAM TESTER" gives wide opportunities for creative fantasy, having in practice slight effect on the production costs of such Program Tester. Let's stress two useful functions in addition to the basic function of testing food combinations as for their correctness.

For the owners of multi-media computers this basic function can b e provided together with special games attracting attention to health prophylaxis through Food Combining.

In "Food Combining Program Tester" designed for any computer the basic function of food testing goes together with a statistic program. Let's explain this idea. Along with health prophylaxis purposes the user of our Software Product simultaneously keeps a diary represented as 2 rows of figures. The first row "marks" the digestive quality of the food combinations used, while the second "marks" how well the user feels within 3–4 hours after the corresponding meal. The correlations ratio of these two rows, automatically calculated with standard statistic techniques demonstrate the usefulness of such health prophylaxis which the user has decided to stick to. The authors of the present patent application are sure that the experience of such users of the claimed Technical Facilities, or, more precisely, the claimed Method of Health Prophylaxis will not be able to contradict to more than half-a-century's experience of Dr. Shelton's non-medicamental practice—they will be only thankful to Dr. Shelton for the improvement of their health.

In conclusion to the above-said the authors hardly dare to express their rather seditious ideas connected with their own unfinished argument on the patentability of their proposed invention. Our deep respect towards the memory of Dr. Shelton did not allow us to begin our application with this statement. The idea is the following:

"Dr. Shelton empowered mankind with the systematized KNOWLEDGE which he approbated in his Health School and proved the EFFECTIVENESS of this knowledge, but he did not define the METHOD to make this knowledge work for MANKIND. Similarly, James Maxwell provided mankind with systematic KNOWLEDGE on electricity and magnetism, showing directly the existence of Lorentz' Force, but neither Maxwell nor Lorentz gave the METHOD to make this knowledge "work" for the mankind, and the ELECTRIC MOTOR appeared later with all its "design components" and "their connections" to become a patentable invention. Our proposed invention could also become a kind of an "electric motor in Food Combining" in the form of a TESTER as easy in utilization, as is an electric motor in a children's toy, so that even a 7-year old boy can use it. Our TESTER, however, does not possess any new "design features"; we can not apply a screw with a screwdriver to our "Electronic Multi-Food Table" which lays the basis for the Tester, that is why our Electronic Table can not be considered a "design component", and our Tester does not fit the "bed of Procrustean" of the Patentability Criteria. That is why, probably, mankind will have to go on reading Dr. Shelton's books, which are luckily translated into nearly all languages of the world without practicing "Health Prophylaxis through Food Combining", as it possesses neither the METHOD nor the TECHNICAL FACILITIES to implement it.

It is fairly easy to prove, even speculatively, that mankind is not aware of "Health Prophylaxis through Food Combining". Let's try to "interview" mankind, asking every man at least 5 questions from Dr. Shelton's books and checking them against Dr. Shelton's recommendations:

1. Do you intentionally avoid eating concentrated protein (like meat, fish, eggs or cheese) at a single meal with concentrated carbohydrate (bread, cereals or potatoes)?
2. Do you intentionally avoid eating starch (i.e. bread or porridge) with sweet products (like jelly, jam, sugar or honey) at a single meal?
3. Do you intentionally avoid eating protein (like meat, fish, eggs or cheese) with fats (i.e. butter or vegetable oil) at a single meal?
4. Do you intentionally avoid eating fruits for dessert?
5. Do you always avoid having milk separately from other food like porridge or bread?

Having received answers from every man, let's sort out all those who said "yes" to all five questions, sum up the number of such people and calculate the percentage of people who are practically concerned about "Health Prophylaxis through Food Combining", at least in the scope of these 5 questions. We are sure that the conclusion will be the following: "No, mankind does not know Health Prophylaxis through Food Combining. Yes, there exist the books and the KNOWLEDGE on the subject, but this knowledge does not exist in peoples' minds. Yes, th e reason of such a situation is the lack of the METHOD of utilization. Yes, the Method exists, although speculatively, but there do not exist the Technical Facilities to implement the speculative Method. Yes, in the age of intormatics it is necessary to widen the bed of Procrustean if people can benefit from it."

With these seditious thoughts the authors, still involved in the discussion, submit the present Patent Application to patent experts, though to some extent in contradiction with Rule 9(iv) of the Instructions PCT, because they use every effort to protect their Method of Health Prophylaxis for the sake of ordinary people and, simultaneously, get an opportunity to implement their Method and further develop it through the above-mentioned "feedback" from the users of the Method.

What is claimed is:

1. A microcomputer apparatus for digestive marking of food combinations and eating manners, comprising:
   (a) memory means for storing information regarding:
      (i) foods databases,
      (ii) a database of food-combining guidelines, and
      (iii) an algorithm for:
         selecting by an user a combination of foods from among those in all foods databases in the memory in order to produce a mark characterizing digestive efficiency of the food combination,
producing the mark for the food combination selected by the user for testing its digestive efficiency, and
presenting the mark for the food combination to the user; and (b) execution means for executing of the algorithm.

2. The microcomputer apparatus according to claim 1, wherein:
(a) the memory means are destined also for storing information regarding:
(i) a database of eating guidelines, and
(ii) an extended algorithm, which further is destined also for:
selecting by the user an eating manner on the basis of all eating guidelines in the memory in order to produce a mark characterizing digestive efficiency of the eating manner,
producing the mark for the eating manner, and
presenting the mark for the eating manner to the user; and
(b) the execution means are destined also for executing of the extended algorithm.

3. The microcomputer apparatus according to claim 2,
(a) wherein the memory means are destined also for receiving and retaining a database of information regarding user's registered eating manners along with its corresponding user's marks based upon indigestion symptoms, a posteriori—after eating by the manners, in order to use the information by a more extended algorithm for further digestive marking of that person's eating manners, and where the database is supplemented by the user in the course of time; and
(b) comprising input means for entering the information into the memory.

4. The microcomputer apparatus according to claim 1 or claim 2 or claim 3,
(a) wherein the memory means are destined also for receiving and retaining information regarding at least one of: a database of user's additional foods and a database of user's additional eating guidelines, in order to use also the information by an once more extended algorithm for further digestive marking, and where the databases are supplemented in the course of time; and
(b) comprising input means for entering the information into the memory.

5. A computer system for digestive marking of food combinations and eating manners, comprising:
(a) a computing device having a memory;
(b) databases in the memory for storing information regarding foods and food-combining guidelines;
(c) an input device for selecting a user, a combination of foods from among those in the foods databases in the memory;
(d) an output device for presenting a mark for the food combination to the user; and
(e) an application program, realizing an algorithm for digestive marking of food combinations, is destined to provide:
selecting by the user, with the aid of the input device, a food combination in order to produce a mark characterizing digestive efficiency of the food combination,
producing, with the aid of the computing device, the mark for the food combination selected by the user for testing its digestive efficiency, and
presenting, with the aid of the output device, the mark for the food combination to the user.

6. The computer system according to claim 5,
(a) comprising also a database, in the memory, relative to eating guidelines; and wherein:
(b) the input device are destined also for selecting by the user an eating manner on the basis of all eating guidelines in the memory;
(c) the output device are destined also for presenting a mark for the eating manner to the user; and
(d) the application program, further realizing an extended algorithm for digestive marking of eating manners, is destined also to provide:
selecting by the user, with the aid of the input device, an eating manner in order to produce a mark characterizing digestive efficiency of the eating manner,
producing, with the aid of the computing device, the mark for the eating manner selected by the user for testing its digestive efficiency, and
presenting, with the aid of the output device, the mark for the eating manner to the user.

7. The computer system according to claim 6,
(a) comprising also a database, in the memory, of information regarding user's registered eating manners along with its corresponding user's marks based upon indigestion symptoms, a posteriori—after eating by the manners, in order to use the information by a more extended algorithm for further digestive marking of that person's eating manners, and where the database is supplemented by the user in the course of time; and wherein:
(b) the input device are destined also for entering the information into the memory; and
(c) the application program, realizing the more extended algorithm, is destined to use the information for further digestive marking of eating manners also.

8. The computer system according to claim 5 or claim 6 or claim 7, comprising:
(a) at least one of: a database, in the memory, of information regarding user's additional foods and a database, in the memory, of information regarding of user's additional eating guidelines, in order to use also the information by an once more extended algorithm for further digestive marking, and where the databases are supplemented in the course of time; and
(b) an input device for entering the information into the memory.

9. A method of digestive marking of food combinations and eating manners, comprising the steps of:
(a) entering, into a memory of a computing device, and retaining, in the memory, databases of information regarding natural foods, classed scientificly for purposes of food combining, and food-combining guidelines as a scientific basis of a base algorithm for digestive marking of food combinations at a single meal;
(b) selecting, with the aid of an input device for the computing device, a combination of foods from among those in the foods databases in the memory in order to produce a mark characterizing digestive efficiency of the food combination;
(c) producing the mark for the food combination with the aid of the computing device which executes the base algorithm based upon standard methods of a mathematical theory of combinations and mathematical statistician as applied to data from the said database for foods and the said database for food-combining guidelines; and (d) presenting, with the aid of an output device for the computing device, the mark for the food combination.

10. The method according to claim 9, further including the steps of:

(a) entering into and retaining in the memory a database of information with regard to eating guidelines as a scientific basis of an extended algorithm now for digestive marking of eating manners, where the eating guidelines as a whole include the food-combining guidelines as a constituent of the whole;

(b) selecting, with the aid of the input device, an eating manner on the basis of all eating guidelines in the memory in order to produce a mark characterizing digestive efficiency of the eating manner as a whole including food-combining as a constituent of the whole;

(c) producing the mark for the eating manner with the aid of the computing device which executes the extended algorithm;

(d) presenting, with the aid of the output device, the mark for the eating manner.

11. The method according to claim 9, further including the step of entering into and retaining in the memory a database of information regarding registered eating manners along with its corresponding marks based upon indigestion symptoms, a posteriori—after eating by the manners, in order to use the information by a more extended algorithm for further digestive marking of eating manners, where the database is supplemented in the course of time.

12. The method according to claim 9 or claim 10 or claim 11, further comprising at least one of: the step of entering into and retaining in the memory a database of information regarding user's additional foods and the step of entering into and retaining in the memory a database of information regarding user's additional eating guidelines, in order to use also the information by an once more extended algorithm for further digestive marking, and where the databases are supplemented in the course of time.

* * * * *